United States Patent [19]

Lucas

[11] 4,042,538

[45] Aug. 16, 1977

[54] SUGAR P-VINYLBENZOYL ESTER AND COPOLYMERS THEREOF

[75] Inventor: Timothy John Lucas, London, England

[73] Assignee: Tate & Lyle Limited, London, England

[21] Appl. No.: 567,140

[22] Filed: Apr. 11, 1975

[30] Foreign Application Priority Data

Apr. 16, 1974 United Kingdom .............. 16579/74

[51] Int. Cl.$^2$ .......................... C07H 15/00; C08L 5/00
[52] U.S. Cl. .................... 260/17.4 SG; 260/17.4 GC; 536/4; 536/115; 536/116; 536/120
[58] Field of Search .................... 260/209 R, 17.4 SG

[56] References Cited

U.S. PATENT DOCUMENTS

| | | | |
|---|---|---|---|
| 2,157,347 | 5/1939 | Reppe et al. .............................. | 260/9 |
| 3,022,285 | 2/1962 | Miller ..................................... | 260/209 |
| 3,127,361 | 3/1964 | Long et al. ............................... | 260/9 |
| 3,400,107 | 9/1968 | Black et al. .............................. | 260/209 |
| 3,440,190 | 4/1969 | Melby ................................. | 260/17.4 SG |

Primary Examiner—Edward M. Woodberry
Attorney, Agent, or Firm—Ostrolenk, Faber, Gerb & Soffen

[57] ABSTRACT

Monosaccharides and disaccharides in which one or more of the hydroxy groups has been replaced by a p-vinylbenzoyloxy group are provided as new compounds. These may be copolymerized with such monomers as styrene or methyl methacrylate to provide novel copolymers.

8 Claims, No Drawings

SUGAR P-VINYLBENZOYL ESTER AND COPOLYMERS THEREOF

The present invention relates to p-vinylbenzoyl ester derivatives of monosaccharides and disaccharides, particularly (but not exclusively) of sucrose. The invention also relates to polymers produced by the copolymerization of these p-vinylbenzoyl derivatives with ethylenically unsaturated copolymerizable monomers. Such derivatives are substantially easier to prepare than are corresponding ether derivatives, e.g. vinyl ether derivatives.

Thus, the present invention consists in derivatives of monosaccharides and disaccharides, in which at least one of the hydroxy groups has been replaced by a p-vinylbenzoyloxy group. The remaining hydroxy groups, if any, of the saccharide may be unsubstituted or substituted by a desired protecting group, e.g. acetyl, or two adjacent hydroxy groups on the saccharide molecule may be substituted by an isopropylidene group.

Preferred derivatives according to the present invention are those of sucrose having the general formula (I), below, and those of α-D-galactopyranose of general formula (II), below.

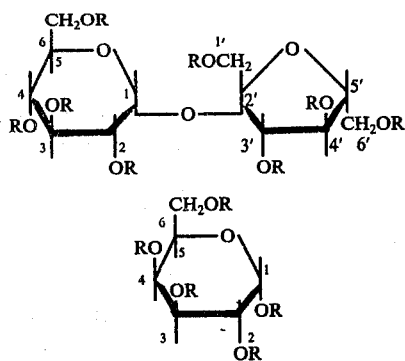

In these formulae, at least one of the symbols R represents a p-vinylbenzoyl group and the other symbols R represent hydrogen or a protecting group. Examples of protecting groups are the acetyl group or, when two adjacent groups represented by symbols R are joined, isopropylidene, benzylidene, ethylidene or chloroethylidene. The preferred compound of formula (I) is 2,3,3',4,4'-penta-O-acetyl-1',6,6'-tri-O-(p-vinylbenzoyl)-sucrose and the preferred compound of formula (II) is 1,2:3,4-di-O-isopropylidene-6-O-(p-vinylbenzoyl)-α-D-galactopyranose.

The sugar derivatives of the present invention may be prepared by reacting a corresponding hydroxy group-containing mono- or di-saccharide with a p-vinylbenzoyl halide, preferably p-vinylbenzoyl chloride. The reaction is most conveniently carried out in a solvent, which should be anhydrous, e.g. anhydrous pyridine. Although the reaction temperature is not critical, the reaction is preferably carried out in the cold, e.g. at a temperature of from the freezing point of the solution to 10° C, preferably about 0° C. If it is desired to direct the p-vinylbenzoyl groups to specific sites on the monosaccharide or disaccharide molecule, then all hydroxy groups except those which it is desired to replace by p-vinylbenzoyloxy groups should be protected, e.g. by acetyl groups. The protected monosaccharide or disaccharide may be prepared by first selectively tritylating hydroxy groups of the saccharide, protecting untritylated hydroxy groups, e.g. by acetylation, detritylating the protected saccharide and then reacting the protected saccharide with the p-vinylbenzoyl halide. If desired, the protecting groups can then be removed by conventional procedures. Tritylation, followed, after reaction with a protecting group, by detritylation, is a convenient way of preparing specific sugar derivatives, since the trityl group can, to some extent, be directed to react at specific sites on the saccharide molecule. This is of particular importance in the case of sucrose, which has eight hydroxy groups and which could, therefore, produce a mixture of many different derivatives.

If the production of specific sugar derivatives is not of importance, then the monosaccharide or disaccharide itself may be reacted directly with the p-vinylbenzoyl halide, to produce a mixture of derivatives, which need not be separated. The relative proportions of the various derivatives in the mixture may be varied by adjustment of the molar ratio of mono- or di-saccharide to p-vinylbenzoyl halide in the reaction mixture. A higher proportion of p-vinylbenzoyl halide will favour the production of more highly substituted derivatives. Individual derivatives can be separated from this mixture by conventional techniques, e.g. by chromatography.

The sugar derivatives of the present invention may be copolymerized with other ethylenically unsaturated monomers, to produce novel polymers containing saccharide units, which polymers also form part of the present invention. We have found that the incorporation of units from these sugar derivatives into polymers of other ethylenically unsaturated monomers, e.g. styrene or methyl methacrylate, increases the glass transition temperature (Tg) of the polymers, which allows them to withstand higher termperatures and thereby enables them to be used more widely, and improves their biodegradeability.

Thus, the present invention further consists in a copolymer of a monosaccharide or of a disaccharide, at least one of whose hydroxy groups has been replaced by a p-vinylbenzoyloxy group, with another ethylenically unsaturated monomer.

If a derivative of a disaccharide, such as sucrose, is used, it is preferably incorporated into the copolymer in an amount not greater than 5 mole percent, more preferably not greater than 2 mole percent (equivalent, in the case of a sucrose derivative, to an amount of from 1 to 15 weight percent). A derivative of a monosaccharide is preferably incorporated into the copolymer in an amount not greater than 10 mole percent, more preferably not greater than 6 mole percent.

Particularly preferred comonomers are styrene and methyl methacrylate, although it will be appreciated that any other ethylenically unsaturated monomer which is copolymerizable with the sugar derivative may be used.

The invention is further illustrated with reference to the following Examples.

EXAMPLE 1

2,3,3',4,4'-Penta-O-actyl-1',6,6'-tri-O-(p-vinylbenzoyl)-sucrose 10 g of 2,3,3',4,4'-penta-O-acetyl-1',6,6'-tri-O-trityl-sucrose (prepared by the method of Brederick et al, Chem. Ber., 1958, 91, 2824) were dissolved in 50 ml of a mixture of chloroform and glacial acetic acid (3:7 by volume). The solution was cooled to 0° C, and 4 ml of glacial acetic acid, which had previously been saturated with dry hydrogen bromide at 0° C, were added dropwise with shaking and cooling. After 10 minutes, the reaction mixture was filtered directly into a flask containing 300 ml of ice water and 8 g of sodium acetate. The solid residue was washed with a little ice cold glacial acetic acid, and the combined filtrate and washings were immediately extracted with chloroform. The extract was washed with ice cold saturated sodium hydrogen carbonate solution until evolution of carbon dioxide ceased, and was then washed with water. After drying the solution and removing the solvent by evaporation under reduced pressure, the residue, in the form of a yellow syrup, was chromatographed on a column of silica gel eluted successively with toluene (1 liter), methyl ethyl ketone/toluene (1 liter, volume ratio 1:5), methyl ethyl ketone/toluene (1 liter, volume ratio 3:10), and methyl ethyl ketone/toluene (1 liter, volume ratio 1:1). Evaporation of the last fraction gave a white solid, which, on recrystallization from chloroform/ether, gave 1.6 g (38%) of 2,3,3',4,4'-penta-O-acetyl-sucrose.

b. 0.25 g of 2,3,3',4,4'-penta-O-acetyl-sucrose was dissolved in anhydrous redistilled pyridine and cooled to 0° C. A solution of 0.2 ml of p-vinylbenzoyl chloride in 1 ml pyridine was added dropwise with cooling and shaking, and the mixture was left for 24 hours. The solvent was then removed by evaporation in vacuo, the residue taken up in chloroform, and this solution washed with aqueous sodium hydrogen carbonate and water. After drying the solution and removing the solvent by evaporation under reduced pressure, the residue was purified by preparative thin layer chromatography to give 2,3,3',4,4'-penta-O-acetyl-1',6,6'-tri-O-(p-vinylbenzoyl)-sucrose as a crisp syrup. The preparative thin layer chromatography was carried out on 20 × 100 cm glass plates coated to a depth of 1.0 mm with an aqueous slurry of Merck $G_F$ 254 silica gel. Bands were located by ultraviolet fluorescence and components were removed by soxhlet extraction with chloroform.

$[\alpha]_D^{25}$ +46.3° (c = 1.0 g per 100 ml, chloroform);
$v_{max}$(nujol) : 1750, 1720, 1625, 1600, 1275, 1220, 1175 cm$^{-1}$;

NMR (100 MHz) : $\tau$ 2.0 - 2.9 (m, 12 protons, 3 $C_6H_4$);
3.0 - 3.7 (d of d 3 protons, 3 —CH=C);
3.9 - 6.1 (m, 20 protons, sucrose ring protons and 3 $CH_2$=C);
7.8 - 8.3 (5s, 15 protons, 5 $CH_3CO$-).

Analysis: Found: C, 62.0%; H, 5.8%; Calculated (for $C_{49}H_{50}O_{19}$): C, 62.4%; H, 5.4%.

EXAMPLE 2

1,2:3,4-Di-O-isopropylidene-6-O-(p-vinylbenzoyl)-α-D-galactopyranose 1,2:3,4-Di-O-isopropylidene-α-D-galactopyranose was prepared by the method of Raymond and Schroeder (J. Amer. Chem. Soc., 1948, 70, 2785). 1 g of this substance was dissolved in anhydrous redistilled pyridine and cooled to 0° C. A solution of 1.5 ml of p-vinyl-benzoyl chloride in pyridine was then added dropwise and the reaction mixture was left for 5 hours. The mixture was then evaporated in vacuo and the residue was taken up in chloroform and washed with sodium hydrogen carbonate solution and then with water. After drying the solution and removing the solvent by evaporation under reduced pressure, the residue was purified by column chromatography on silica gel eluted with chloroform to give 1.4 g (93%) of 1,2:3,4-di-O-isopropylidene-6-O-(p-vinylbenzoyl)-α-D-galactopyranose.

$[\alpha]_D^{25}$ —48.8° (c = 1.0 g per 100 ml, chloroform);
$v_{max}$(film): 1720, 1625, 1600, 1570, 1450, 1385, 1275, 1220, 1170, 1100, 1060, 1000, 920, 900, 850 cm$^{-1}$.

NMR (100 MHz) $\tau$ : 2.0 - 2.9 (m, 4 protons, $C_6H_4$);
3.0 - 3.7 (d of d, 1 proton, $J_{1,2a}$ = 11 Hz, $J_{1,2b}$ = 18 Hz, —CH=C);
4.1 (d, 1 proton, H-1, $J_{1,2}$ = 1.5 Hz);
6.5 (d of d, 1 proton, H-2, $J_{1,2}$ = 1.5 Hz, $J_{2,3}$ = 24 Hz);
4.5, 4.6 (2s, 2 protons, H-6, H-6');
5.3 - 6.2 (m, 5 protons, H-3, H-4, H-5, $CH_2$=C );
8.6, 8.8 (2s, 12 protons, 2($CH_3)_2C$=).

Analysis: Found: C, 65.1%; H, 6.95%; Calculated (for $C_{21}H_{26}O_7$): C, 64.6%; H, 6.7%.

EXAMPLE 3

Mixture of O-(p-vinylbenzoyl)-sucrose derivatives

Sucrose was dissolved in anhydrous redistilled pyridine and the solution was cooled to 0° C. 1 equivalent of p-vinylbenzoyl chloride, also in pyridine at 0° C, was added. The mixture was allowed to come to room temperature and was kept in the dark. No attempt was made to isolate any products, as the solution certainly contained a mixture of products.

EXAMPLE 4

Mixture of O-(p-vinylbenzoyl)-sucrose derivatives

The procedure described in Example 3 was repeated, except that 3 equivalents of p-vinylbenzoyl chloride were used, giving a solution containing a mixture of O-(p-vinylbenzoyl)-sucrose derivatives.

EXAMPLE 5

Styrene-sucrose derivative copolymers

Styrene and 2,3,3',4,4'-penta-O-acetyl-1',6,6'-tri-O-(p-vinylbenzoyl)-sucrose in benzene solution were copolymerized in various proportions in sealed ampoules under nitrogen with 1 mole percent of azobisisobutyronitrile at 60° C. The copolymers were precipitated into cooled methanol, filtered and washed with methanol, and then dried in vacuo. For purposes of comparison, the procedure was repeated omitting the sucrose derivative. The proportion of sucrose derivative in the reactants, as well as the proportion incorporated into the copolymer as estimated by optical rotation and by microanalysis, is shown in Table I.

Table 1

| | | Sucrose Deriv. in Polymer (mole %) | |
|---|---|---|---|
| Exp. No. | Sucrose Deriv. in Reactants (mole %) | from optical rotations | from microanalysis |
| 1 | 0 | — | 0.00 |
| 2 | 0.11 | * | 0.19 |
| 3 | 0.58 | 0.44 | 0.69 |
| 4 | 1.10 | 1.51 | 2.11 |
| 5 | 1.91 | 1.99 | 2.08 |

*Optical rotation too small for accurate measurement

The glass transition temperatures of the copolymers were determined by differential scanning calorimetry and found for Experiments 2, 3, 4 and 5 to be 90.3° C, 92.5° C, 94.4° C and 90.3° C, respectively (heating rate 1° C per minute). The glass transition temperature of polystyrene itself is about 80° C.

EXAMPLE 6

Copolymers containing mixtures of sucrose derivatives

Styrene and methylmethacrylate were copolymerized with the sucrose derivative mixtures prepared in Examples 3 and 4 in various proportions. The sucrose derivative mixtures were used as prepared, i.e. in solution in pyridine. Otherwise, the procedure was as described in Example 5, although further addition of pyridine was necessary with higher initial ratios of sucrose derivatives, in order to maintain these derivatives in solution. The products were then isolated by precipitation into cold methanol. The proportions of monomers used and the glass transition temperatures of the products are shown in Table II.

Table II

| Exp. No. | Comonomer (1) | Mixture of Ex. | Volume of Sucrose Deriv. mixture (ml) | Tg° C (2) |
|---|---|---|---|---|
| 6 | St | 3 | 1 | 93.5 |
| 7 | St | 3 | 2 | 93.5 |
| 8 | St | 3 | 3 | 94.0 |
| 9 | St | 3 | 5 | 96.2 |
| 10 | St | 3 | 10 | 99.3 |
| 11 | St | 4 | 1 | 98.4 |
| 12 | St | 4 | 2 | 100.6 |
| 13 | St | 4 | 3 | 101.1 |
| 14 | St | 4 | 5 | 102.0 |
| 15 | St | 4 | 10 | 111.6 |
| 16 | MMA | 3 | 1 | 113.5 |
| 17 | MMA | 3 | 2 | 116.0 |
| 18 | MMA | 3 | 3 | 120.0 |
| 19 | MMA | 3 | 5 | 120.5 |
| 20 | MMA | 3 | 10 | (Note 3) |
| 21 | MMA | 4 | 1 | 117.5 |
| 22 | MMA | 4 | 2 | 119.5 |
| 23 | MMA | 4 | 3 | 122.0 |
| 24 | MMA | 4 | 5 | 123.0 |
| 25 | MMA | 4 | 10 | 126.0 |

Notes: (1) St = styrene MMA = methylmethacrylate.

2. Tg determined by differential scanning calorimetry at a heating rate of 8° C per minute for the styrene copolymers and 20° C per minute for the methylmethacrylate copolymers.

3. Sample very brittle and highly discoloured; no measurement was made since good thermal contact with the instrument was impossible.

In a test for biodegradeability, in which polymers were immersed in a fungus suspension, the weight loss of a methylmethacrylate/sucrose derivative mixture copolymer after 28 days was more than twice that of a methylmethacrylate homopolymer.

EXAMPLE 7

Styrene-galactopyranose derivative copolymers

Copolymers of 1,2:3,4-di-O-isopropylidene-6-O-(p-vinylbenzoyl)-α-D-galactopyranose with styrene were prepared by the process described in Example 5, varying the initial proportion of galactopyranose derivative from 1.5 to 10 mole percent. The initial proportion of galactopyranose derivative in the monomer mixture, as well as the proportion of galactopyranose derivative units in the final polymer are shown in Table III.

Table III

| Exp. No. | Mole % Galactopyranose Derivative | |
|---|---|---|
| | In Reactants | In Polymer |
| 26 | 1.50 | 1.52 |
| 27 | 3.00 | 3.54 |
| 28 | 6.00 | 4.40 |
| 29 | 10.00 | 5.95 |

The quantity of galactopryanose derivative in the polymer was determined from optical rotation measurements.

I claim:

1. A derivative of a sugar selected from the group consisting of monosaccharides and disaccharides, in which at least one of the hydroxy groups of said sugar has been replaced by a p-vinylbenzoyloxy group.

2. Derivative as claimed in claim 1, wherein said sugar is sucrose.

3. Derivative as claimed in claim 1, wherein said sugar is α-D-galactopyranose.

4. 2,3,3′,4,4′-Penta-O-acetyl-1′,6,6′-tri-O-(p-vinylbenzoyl)sucrose.

5. 1,2:3,4-di-O-isopropylidene-6-O-(p-vinylbenzoyl)-α-D-galactopyranose.

6. Sucrose derivative of the formula

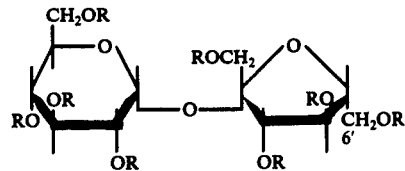

wherein each R is independently selective from the group consisting of hydrogen, p-vinylbenzoyl and a protecting group, at least one R being p-vinylbenzoyl.

7. α-D-galactopyranose derivative of the formula:

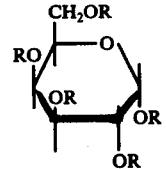

wherein each R is independently selective from the group consisting of hydrogen, p-vinylbenzoyl and a protecting group, at least one R being p-vinylbenzoyl.

8. A copolymer of an ethylenically unsaturated sugar derivative with another ethylenically unsaturated monomer, where in the sugar derivative is selected from the group of monosaccharides and disaccharides having at least one of their hydroxy groups replaced by a p-vinyl benzoyloxy group, and wherein the sugar derivative is present in the copolymer in an amount not greater than 5 mole percent when it is a derivative of a disaccharide and not greater than 10 mole percent when it is a derivative of a monosaccharide, and where in said another ethylenically unsaturated monomer is styrene or methyl methacrylate and wherein the copolymer has a glass transition temperature of 90.3° to 126° C.

* * * * *